United States Patent [19]

Glassman

[11] 4,019,517
[45] Apr. 26, 1977

[54] DISPOSABLE DIAPER

[76] Inventor: Jacob A. Glassman, 1680 Meridian Ave., Miami Beach, Fla. 33139

[22] Filed: July 2, 1975

[21] Appl. No.: 592,406

[52] U.S. Cl. .............................. 128/284; 128/290 R
[51] Int. Cl.² ........................................ A61F 13/16
[58] Field of Search ............... 128/284, 287, 290 R, 128/290 H, 290 W

[56] References Cited

UNITED STATES PATENTS

| | | | |
|---|---|---|---|
| 2,122,417 | 7/1938 | Fridolph | 128/284 |
| 2,476,869 | 7/1949 | Hughes | 128/284 |
| 2,591,079 | 4/1952 | Leaton | 128/284 |
| 2,815,026 | 12/1957 | Meyer | 128/284 |
| 2,840,078 | 6/1958 | Smith | 128/290 H |
| 3,042,043 | 7/1962 | Wuhrlin | 128/284 |
| 3,050,063 | 8/1962 | Margraf | 128/284 |
| 3,110,312 | 11/1963 | Wirth | 128/287 |
| 3,162,196 | 12/1964 | Salk | 128/287 |
| 3,595,235 | 7/1971 | Jespersen | 128/284 |
| 3,636,952 | 1/1972 | George | 128/287 |
| 3,794,034 | 2/1974 | Jones, Sr. | 128/290 R |

*Primary Examiner*—Aldrich F. Medbery
*Attorney, Agent, or Firm*—Elmer L. Zwickel

[57] ABSTRACT

A double duty disposable diaper comprised of a bottom moisture impervious layer of thin material having one or more layers of absorbent material arranged thereon face to face, and a strip comprised of like layers of material centrally arranged on the absorbent layer midway between its side edges. The insert strip extends to or beyond at least one edge of said absorbent layer and is detachably secured to said layer. At least one absorbent layer of the diaper assembly may be impregnated with medication or a deodorant. The invention also embodies the method of fabricating such a diaper.

5 Claims, 7 Drawing Figures

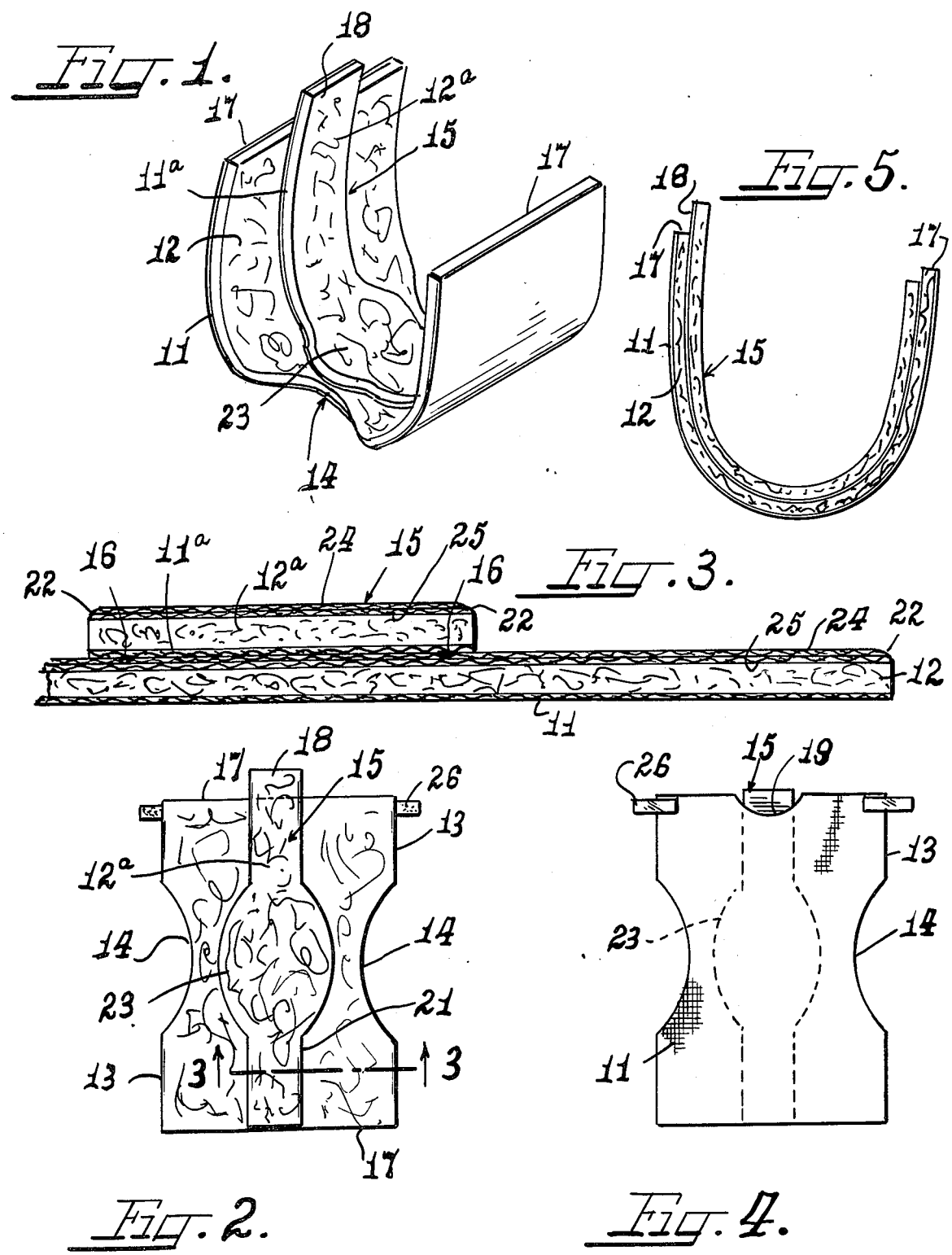

DISPOSABLE DIAPER

The invention relates to improvements in disposable diapers and is characterized by having a removable insert strip of absorbent material overlying a moisture insulated layer in the longitudinal central area of a main diaper and arranged in such manner that, when wetted or soiled, it can be readily removed without undoing or removing the main diaper, thus leaving the retained main diaper relatively dry for further use.

Heretofore, disposable diapers have embodied a one-piece structute comprised of an outer moisture impervious sheet of material and an inner layer or layers of moisture absorbent material, all of substantially uniform size. In use, when such a diaper became wetted or soiled and therefore unsuited for further use, the entire diaper had to be replaced by a dry diaper. This proceedure is annoying not only to the wearer but also to the attendant who must change the diaper. According to the present invention the main diaper is fitted with a readily removable centrally located inner absorbent layer of considerably less width than the main diaper but of a length that locates at least one end thereof in position to be readily grasped for pulling out the insert strip which is, in fact, in the form of an elongated member extending from front to back of the main diaper when it is being worn. This enables the attendant, upon observance that the insert strip has become wetted or soiled, to grasp the insert strip and gently pull it out and away from the main diaper without diaper removal, hence the wearer is not disturbed and the attendant is saved the need to change diapers inasmuch as the main diaper, after removal of the soiled insert strip, is still relatively dry and hence has a prolonged serviceable life.

It is therefore an object of the invention to provide a diaper of the character referred to.

Another object is to provide a diaper with a removable insert.

Another object is to provide a diaper with a removable insert, which diaper is substantially form fitting.

Another object is to provide a diaper and attached insert strip with chamfered edges so as to avoid skin irritation.

Another object is to provide a diaper with a removable insert, wherein means is provided to facilitate gripping of the insert for withdrawing same from the main diaper.

Another object is to provide a diaper with recessed side edges to allow for form fitting and minimize wrinkling while being worn.

Another object is to provide a novel method for fabricating a diaper having a removable insert therein.

Other objects and advantages of the invention will become apparent with reference to the following description and accompanying drawings.

IN THE DRAWINGS

FIG. 1 is a perspective view of the improved diaper.

FIG. 2 is a plan view of the inside face of the diaper.

FIG. 3 is a fragmentary sectional view taken substantially on line 3—3 of FIG. 2.

FIG. 4 is an outside view of a modified form of diaper.

FIG. 5 is a side elevational view of the diaper shown in FIG. 1.

Figure 6:
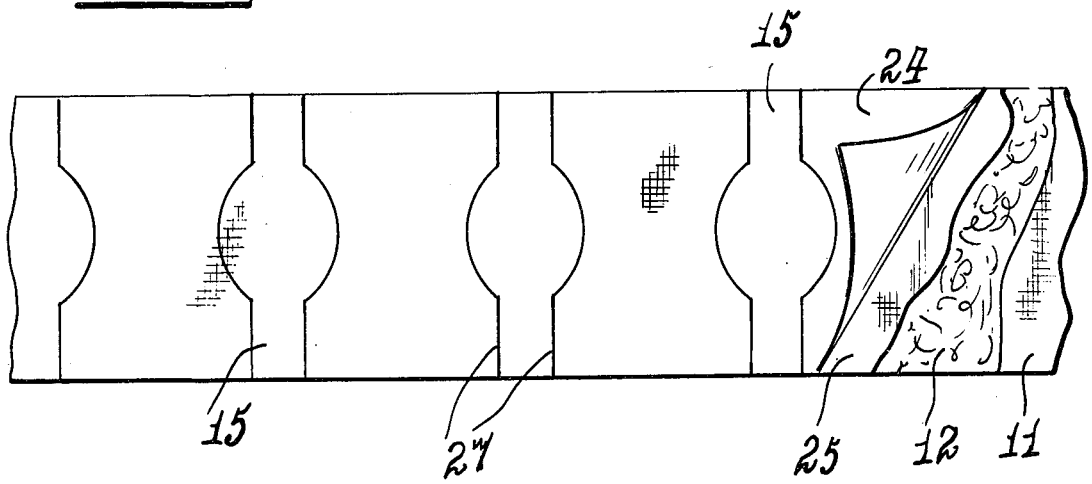
FIG. 6 is a plan view of a strip showing the manner of cutting diapers and inserts therefrom.

Referring now to the representative illustrations of the improved diaper, as shown in the accompanying drawings, the diaper is comprised of an outer moisture impervious layer of sheet material 11. Arranged on the top surface of said sheet in face to face contact therewith, is a relatively thick layer 12 of highly moisture absorbent material, such as cotton, cellulose, crim or the like. These two layers are of like size and have preferably rectangular shape, and are secured together along their complemental edges thus to form a main diaper having a longitudinal central portion or area. The complemental side edges 13 of the two joined layers are suitably recessed, as at 14, so that when the diaper is being worn there is no or at most but a minimum amount of compression sidewise between the thighs thus eliminating or minimizing wrinkling, gaping and bulging.

An insert strip 15 comprised of a bottom layer of moisture impervious material 11a and an overlying layer 12a of highly moisture absorbing material secured together along complemental edges, laid over the diaper layer 12 and preferably is lightly secured to said layer 12 by spot adhesive 16 or by heat or compression. This attachment is readily rupturable for a purpose to be explained presently. The insert strip 15 preferably has length slightly greater than that of the longitudinal central portion or area of the aforesaid main disper, which according to the FIG. 2 embodiment, is the distance between the two end edges 17 of the diaper portion 11, 12, so that when in place at least one end projects beyond an end edge 17 to provide a tab 18 which can be grasped between the fingers when removal of the insert strip 15 is advisable. In the alternative, one end edge 17 of the diaper portion 11, 12, can be recessed, as at 19 (FIG. 4) to afford access to the insert strip for finger grasping engagement and removal. Preferably, the side and end edges 13 and 17 of the absorbent layer 12 and the side edges 21 of the insert strip are rounded on their upper extremeties, as at 22, so as to present a smooth non-irritating surface. As shown, the insert strip 15 is arranged substantially midway between the diaper side edges 13 and preferably has a wide medial area 23.

In some instances a thin layer of moisture absorbent material 24 may be arranged on top of the absorbent layer 12, 12a, and further, a thin absorbent layer 25 impregnated with a deodorant or medication may be interposed between the absorbent layers 12, 12a and the overlying layer 24.

In use, the diaper, with the insert strip 15 in place on the longitudinal central portion of the main diaper, is fitted onto the wearer and may be secured by pins or by means of adhesive tabs 26. When the absorbent layer 12a of the insert strip 15 becomes wetted or soiled, the attendant may grasp the exposed end 18 of said strip and by the application of a slight tug can separate said insert strip from the main diaper 11, 12, and withdraw said strip. As a consequence, the clean unsoiled or non-wetted main diaper remains in place and in effect constitutes a clean diaper. Thus, the diaper is in effect a double-duty diaper, the need to change frequently is cut in half and the wearer is undisturbed by the withdrawal of the insert strip. This is particularly advantageous when the wearer is sleeping.

Figure 7:
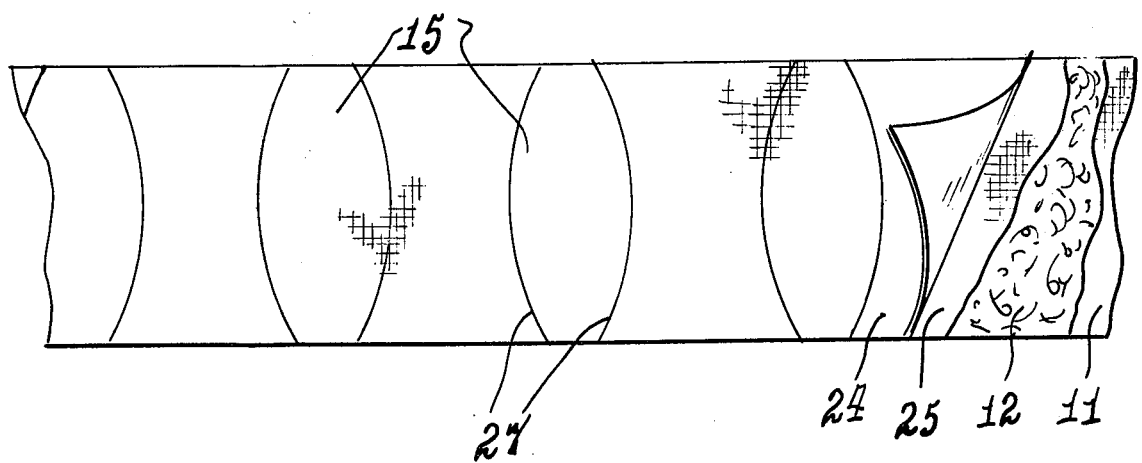
FIG. 7 is a plan view of a strip showing another form of cutting diapers and inserts therefrom.

The total diaper may be fabricated from a single strip of material comprised of the moisture impervious outer layer 11 and the inner absorbent layer 12, with or without the addative layers 24, 25, suitably cut along lines 27, as illustrated in FIGS. 6 and 7.

Although I have described a preferred embodiment of the invention in considerable detail, it will be understood that the description thereof is intended to be illustrative rather than restrictive, as details of the structure can be modified or changed without departing from the spirit or scope of the invention.

I claim:

1. A double-duty diaper comprising, in combination, a main diaper including at least one relatively thick, substantially rectangular layer of highly moisture-absorbent material having a longitudinal central portion, an insert strip of less width than the main diaper also of highly moisture absorbent material superimposed on said longitudinal central portion of and being lightly adhered to the inner surface of said one layer, means carried by the main diaper for securing same about the waist portion of a human body with said insert strip in position to contact the body, and means for removing said insert strip from the main diaper without corresponding removal of or impairment of the diapering potential of said main diaper comprising said insert strip having length greater than that of the longitudinal central portion of the main diaper whereby at least one end of the insert strip extends as a pull tab beyond a related end edge of the main diaper.

2. A double-duty diaper according to claim 1, wherein said related end edge of the main diaper extends straightway across said diaper, and said one end of the insert strip extends beyond said straightway extending end edge.

3. A double-duty diaper according to claim 1 wherein said related end edge of the main diaper has a recess disposed midway of the length of said related end edge into which the said pull tab end of the insert strip extends.

4. A double-duty diaper according to claim 1 wherein the side edges of said main diaper-forming layer of highly moisture absorbent material each has a recess provided in its mid-length portion as effects narrowing thereof throughout the extent of said mid-length portion, and said insert strip has width in its mid-length portion corresponding substantially to the width of the recessed mid-length portion of the main diaper.

5. The method of fabricating a double duty diaper comprising the steps of superimposing on the body-contacting surface of a thick layer of highly mositure-absorbent material providing a main diaper having a longitudinal central portion, an insert strip also of highly moisture-absorbent material and which has less width than that of said thick layer and length greater than the length of said longitudinal central portion thereof, and positioning said insert strip centrally of and longitudinally with respect to said main diaper-forming layer so that at least one end of the insert strip projects beyond the related end edge of the said layer, thereby to provide a pull tab enabling withdrawal of the insert strip upon wetting or soiling thereof from said main diaper-forming layer without any lessening of the diapering potential of said layer.

* * * * *